United States Patent [19]

Reipur

[11] Patent Number: 4,651,760
[45] Date of Patent: Mar. 24, 1987

[54] TOOTHPICK

[76] Inventor: John Reipur, Frisersvej 2A, DK-2920 Charlottenlund, Denmark

[21] Appl. No.: 711,572

[22] PCT Filed: Jun. 25, 1984

[86] PCT No.: PCT/DK84/00059
§ 371 Date: Feb. 28, 1985
§ 102(e) Date: Feb. 28, 1985

[87] PCT Pub. No.: WO85/00101
PCT Pub. Date: Jan. 17, 1985

[30] Foreign Application Priority Data

Jun. 28, 1983 [DK] Denmark ............................ 2960/83

[51] Int. Cl.⁴ .............................................. A61C 15/00
[52] U.S. Cl. ........................................... 132/89; 132/93
[58] Field of Search .............................. 132/89, 90, 93

[56] References Cited

U.S. PATENT DOCUMENTS

| 973,842 | 10/1910 | Baird. | |
|---|---|---|---|
| 1,451,380 | 10/1923 | Thum. | |
| 3,910,293 | 7/1975 | Lemelson | 132/89 |
| 4,271,854 | 9/1981 | Bengtsson | 132/89 |
| 4,314,574 | 9/1982 | Inerte | 132/89 |

FOREIGN PATENT DOCUMENTS

| 83/3054638 | 9/1983 | European Pat. Off.. | |
|---|---|---|---|
| 83/8105062 | 11/1983 | European Pat. Off.. | |
| 1101693 | 9/1959 | Fed. Rep. of Germany. | |
| 1084872 | 12/1960 | Fed. Rep. of Germany. | |
| 37199 | 12/1968 | Finland. | |
| 1269529 | 7/1961 | France | 132/93 |
| 425141 | 9/1982 | Sweden. | |

Primary Examiner—Gene Mancene
Assistant Examiner—Cary E. Stone
Attorney, Agent, or Firm—Kenyon & Kenyon

[57] ABSTRACT

A toothpick made from plastic for manual removal of film on teeth and for stimulation of the gum is upwardly curved at its pointed end portion (1) to prevent the pointed end from penetrating the gum, which may often occur, especially in case of negative papillae. Furthermore an underlying, longitudinal notch (3) is provided above the back portion (4), which allows the toothpick to be compressed in its transverse direction, and which moreover allows room for the gum in case of normal as well as damaged papillae.

Furthermore, transverse flaps (5) on both sides of the toothpick are provided, in order that these may strike the tooth surfaces efficiently, even where particles from repair work on teeth may remain and fill the spaces between the teeth. To facilitate easy orientation and operation, the toothpick has been provided with an upwardly projecting plate (6) towards its rear portion.

5 Claims, 3 Drawing Figures

TOOTHPICK

BACKGROUND OF THE INVENTION

1. Field of the Invention

The present invention relates to a toothpick made from plastic in the shape of an oblong body with an essentially triangular cross section, which body decreases in size towards a pointed end portion, and which body manually can be inserted in interproximal cavities.

2. Description of the Prior Art

Toothpicks are used for stimulation of the gum, for removing film on teeth, for removing food particles in interproximal cavities and for similar dental hygienic purposes. Removal of tooth film, covering the teeth in the area towards the gum margin, is particularly important for preventing caries and parandentosis.

The usual shape of a toothpick is a protracted body with a relatively small sectional area with triangular shape for insertion in the mouth in order that it by manual control can strike the teeth and gum and serve its purpose, i.e. to clean and stimulate the gum. While in use the toothpick is held between the fingers and is manipulated to produce the necessary movement.

The hitherto known toothpicks are straight and are made of wood, metal or plastic. They are inserted into the space between neighbouring teeth and are pressed so hard that the sides of the toothpick strikes the sides of the teeth. For the toothpick to withstand this it should possess a certain amount of strength and rigidity to be strong enough in its longitudinal direction. The toothpick cannot easily be compressed in its transverse direction and thus it cannot adjust its shape to the cavity to be cleaned, and it will also tend to break while in use. Thus such toothpicks tend to damage the gum and may occasionally do more harm than good. Especially where negative papillae occur, damage of the gum may easily occur, as the pointed end of the toothpick easily penetrates the skin and damages this. Moreover, it is difficult and often even impossible to apply toothpicks in the area of the back of the mouth as it is not possible to insert a toothpick from the side of the tongue.

Thus an efficient cleaning of the tooth surfaces, in order that all bacteria film is removed efficiently from these surfaces and in order to stimulate the gum, cannot be achieved by the hitherto known toothpicks.

SUMMARY OF THE INVENTION

It is the object of the present invention to overcome these disadvantages of the hitherto known toothpicks and at the same time to aim at an efficient cleaning and stimulation without causing damage to teeth or gum, and this is achieved by means of a toothpick which has a pointed end that curves upwardly from the under side of the toothpick. Thus, in a simple way and by simple means, a toothpick is achieved that may easily be inserted into the interproximal cavities without the pointed end penetrating the gum even where negative papillae occur, as the pointed end being inserted horizontally points upwards, and like a ski or runner slides across the top of the gum without damaging the parts of the gum projecting upwardly on both sides of the cavity. Thus a considerable risk of damaging the gum when using the toothpick is eliminated.

By supplying the toothpick with a notch along the under side, the gum with normal papil is protected, as there is room for the gum in the notch while the toothpick is being inserted and used.

By decreasing the size of the notch towards the front portion of the toothpick, an expedient material distribution is achieved without causing damage to the gum, the notch being narrower and the sectional area of the toothpick becoming smaller.

By making the toothpick compressible in its transverse direction at its widest point, it may be applied even if the papil is damaged or repair particles from bridges, crowns and fillings remain, or if the cavity is otherwise narrowed.

By supplying the toothpick with transverse, yielding flaps, an efficient remocval of film on teeth surfaces is achieved above all, as the flaps will strike along all sides of the teeth, even at places where particles of repair material or the like remain. Furthermore, when the toothpick is being operated in a longitudinal direction, the flaps will clean the side of the teeth towards the tongue just as efficiently as the side towards the cheek. Thus a hitherto unknown efficient cleaning of the tooth surfaces is achieved when treating the teeth by means of a toothpick inserted from the outer side. Moreover, the flaps ensure a good rigidity of the toothpick, avoiding any tendency to twist while in use.

Finally it is expedient, to supply the toothpick with an upwardly projecting plate facilitating easy orientation and operation.

BRIEF DESCRIPTION OF THE DRAWING

In the following the invention will be described in more detail with reference to the drawing, where.

DESCRIPTION OF THE PREFERRED EMBODIMENT

Figure 1:
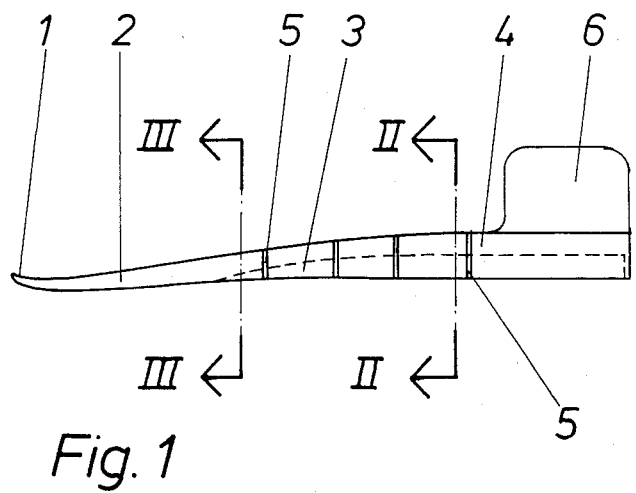
FIG. 1 shows a toothpick seen from the side.

FIG. 1 shows an example of an embodiment of a toothpick. It is made of plastic in one piece by generally known die casting.

Figure 2:
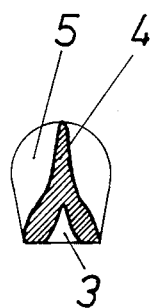
FIG. 2 shows a sectional view, seen in the direction along II—II in FIG. 1.
Figure 3:
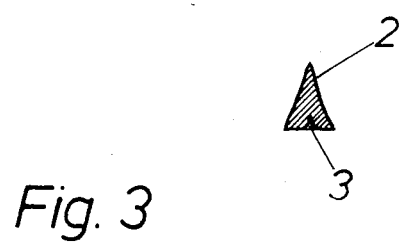
FIG. 3 shows a sectional view, seen in the direction along III—III in FIG. 1.

The cross section of the protracted body 4 has, as appears from FIGS. 2 and 3, a triangular shape, the largest dimension of which being towards the rear. This largest dimension extends for a distance corresponding to one third of the full length of the toothpick.

From this point to the front portion 2 of the toothpick the dimension decreases evenly to a point about ⅔ from the back portion. The under side is even along the whole of this piece, and moreover a notch 3 is provided on the under side in the length of this piece running along the middle, as appears from FIG. 2. The object of this notch 3 is that the toothpick can be compressed at its widest point. While the under side is level, the height of the toothpick decreases evenly along the middle third of the length.

At the front portion 2 the under side is slightly convex, but at the pointed end 1 it curves upwardly to produce the shape of a ski or runner, as is seen in FIG. 1. In this front portion 2 there is no need for a notch, the sectional area being so small that the pointed end 1, 2 can easily enter the interproximal cavity.

At the middle portion of the toothpick a number of flaps 5 are provided running from the bottom edge up to the top edge on both sides, as is seen in FIG. 2. These flaps may be of different outer configuration according to usage. Each set of flaps may thus be of alternating shape, and their number may vary according to usage. These flaps 5 strike the opposed tooth surfaces efficiently during insertion as well as during removal, and due to their yielding capacity they can adjust themselves to the shape of the cavity in order that optimal cleaning is achieved.

Moreover, the flaps 5 will ensure that the toothpick attains a considerable rigidity and that it will keep its shape to a very high degree even though it may be twisted in use.

Finally an operating part 6 in the form of a plate is provided to facilitate the use of the toothpick, which partly ensures correct handling during the insertion in the cavity and partly facilitates the operation where a longitudinal movement and perhaps a sideways change of direction is to be made.

The toothpick is made of a harmless, synthetic resinous polymeric material like polystyrene or another thermoplastic material. The toothpick may be produced with special physical characteristics such as a particular surface structure, hardness, elasticity or rigidity.

The size of the toothpick can typically be a length of approx. 5 cm, largest width of approx. 3 mm and maximum height of approx. 4 mm, to which should be added the operating part which may be of a height of approx. 1 cm.

I claim:

1. A toothpick made of plastic, the toothpick having an elongated body with a first end portion, a second end portion opposite the first end portion, a base surface having two spaced apart longitudinal edges, and two side surfaces converging from the spaced apart longitudinal edges of the base surface to a thin longitudinal edge opposite the base surface to define an essentially triangular cross section for said body, the cross-sectional area of said body decreasing progressively in said first end portion towards a pointed tip which can be manually inserted into interproximal cavities between adjacent teeth with the base surface facing the gum margin, wherein the improvement comprises said thin longitudinal edge in the first end portion being curved away from the side of the base surface to terminate at said pointed tip, so that said tip is directed away from and will not penetrate the gum surface when the toothpick is inserted interproximally with the base surface facing the gum margin, and at least one flexible flap extending transversely to the longitudinal dimension of the body outward from each side surface of the body from the respective one of the two spaced apart longitudinal edges to the thin longitudinal edge at the junction of the converging side surfaces.

2. A toothpick according to claim 1 wherein a longitudinal notch is formed in said base surface at least along a part of the body intermediate the first and second end portions to impart lateral flexibility to the two spaced apart longitudinal edges of the base surface.

3. A toothpick according to claim 2 wherein said notch decreases in cross-sectional area towards the first end portion of the body.

4. A toothpick according to claim 2 or 3 wherein said notch does not extend into the first end portion of the body.

5. A toothpick according to claim 1 further comprising a flaplike operating part extending away from the thin longitudinal edge at the second end portion of the body to facilitate manual grasping of the toothpick.

* * * * *

UNITED STATES PATENT AND TRADEMARK OFFICE
CERTIFICATE OF CORRECTION

PATENT NO. : 4,651,760

DATED : 24 March 1987

INVENTOR(S) : John REIPUR

It is certified that error appears in the above-identified patent and that said Letters Patent is hereby corrected as shown below:

```
Col. 1, lines 21 and 22:  change "it by manual control" to
                          --by manual control it--.
Col. 1, line 29:  change "strikes" to --strike--.
Col. 2, line 14:  change "remocval" to --removal--.
Col. 2, line 14:  change "teeth" to --tooth--.
```

Signed and Sealed this

Sixth Day of October, 1987

Attest:

DONALD J. QUIGG

Attesting Officer

Commissioner of Patents and Trademarks